United States Patent
Zhang et al.

(10) Patent No.: US 6,504,071 B2
(45) Date of Patent: Jan. 7, 2003

(54) PROCESS AND APPARATUS FOR PREPARATION OF ETHYLBENZENE BY ALKYLATION OF BENZENE WITH DILUTE ETHYLENE CONTAINED IN DRY GAS BY CATALYTIC DISTILLATION

(75) Inventors: Jirui Zhang, Beijing (CN); Dongfeng Li, Beijing (CN); Jiquan Fu, Beijing (CN); Gang Cao, Beijing (CN)

(73) Assignee: Beijing Institute of Clothing Technology, Beijing (CN)

( * ) Notice: Subject to any disclaimer, the term of this patent is extended or adjusted under 35 U.S.C. 154(b) by 0 days.

(21) Appl. No.: 09/732,918

(22) Filed: Dec. 11, 2000

(65) Prior Publication Data

US 2001/0018545 A1 Aug. 30, 2001

(30) Foreign Application Priority Data

Dec. 10, 1999 (CN) .......................... 99124797 A

(51) Int. Cl.[7] .......................... C07C 2/68; C07C 15/067
(52) U.S. Cl. .................. 585/467; 585/448; 203/DIG. 6
(58) Field of Search ............................... 585/467, 448; 203/DIG. 6

(56) References Cited

U.S. PATENT DOCUMENTS

| | | | |
|---|---|---|---|
| 5,030,786 A | 7/1991 | Shamshoum et al. | 585/467 |
| 5,118,896 A | * 6/1992 | Steigelmann et al. | 585/467 |
| 5,145,817 A | 9/1992 | Sherrod | 502/65 |
| 5,476,978 A | 12/1995 | Smith, Jr. et al. | 585/323 |
| 5,756,872 A | * 5/1998 | Smith et al. | 585/323 |

FOREIGN PATENT DOCUMENTS

| | | |
|---|---|---|
| CN | 1031072 A | 2/1989 |
| CN | 1074392 A | 7/1993 |
| CN | 1096470 A | 12/1994 |
| CN | 1207960 A | 2/1999 |
| EP | 0 308 097 | 3/1989 |
| EP | 0 308 099 | 3/1989 |

OTHER PUBLICATIONS

Bellussi et al.; "Liquid–Phase Alkylation of Benzene With Light Olefins Catalyzed by β Zeolites", Journal of Catalysis, vol. 157, pp. 227–234, (1995).

"Petrochemical Processes '95", Hydrocarbon Processing, pp. 110 and 114, (1995).

* cited by examiner

Primary Examiner—Thuan D. Dang
(74) Attorney, Agent, or Firm—Finnegan, Henderson, Farabow, Garrett & Dunner, L.L.P.

(57) ABSTRACT

A new process for the preparation of ethylbenzene by alkylation of benzene with dilute ethylene contained in dry gas by catalytic distillation and the apparatus used therefor are disclosed. The new process includes the pretreatment of raw refinery dry gas, the gas-liquid-solid three phases alkylation of benzene with the ethylene over a solid catalyst in a catalytic distillation tower, and concurring course of distillation separation of product mixture. The performance, type, and loading way of catalyst and distillation packing should satisfy the given requirements. The invention has many advantages such as simple apparatus structure and ease in operation, moderate operation conditions, large catalyst capacity, high product quality, long catalyst lifetime, etc.

11 Claims, 3 Drawing Sheets

PROCESS AND APPARATUS FOR PREPARATION OF ETHYLBENZENE BY ALKYLATION OF BENZENE WITH DILUTE ETHYLENE CONTAINED IN DRY GAS BY CATALYTIC DISTILLATION

FIELD OF THE INVENTION

The present invention relates to a process for the preparation of ethylbenzene by alkylation of benzene with dilute ethylene contained in refinery dry gas. More particularly, the invention relates to a process for the preparation of ethylbenzene by alkylation of benzene with dilute ethylene contained in dry gas by catalytic distillation, also to an apparatus used for the catalytic distillation process.

RELATED ART

Ethylbenzene is an important organic chemical material which is mainly used to produce styrene. The vigorous market need for styrene brings along the continued increase of ethylbenzene production. Therefore, it is of great importance to find out new material sources and cheaper route for ethylbenzene preparation.

As the main raw material in production of styrene monomer, almost 90% of ethylbenzene are produced by the alkylation of benzene with pure ethylene. The ethylene source is very important for the development of ethylbenzene industry, which has a bearing on the economic effectiveness of ethylbenzene industry and on smoothing operation. Making full use of various ethylene sources, especially dilute ethylene, will certainly expand the output of ethylbenzene production.

Catalytic cracking is an important process for deep transformation of heavy oil in refineries which produces dry gas containing a dilute ethylene in an amount of about 10–20% by mole. Most of dry gas are used as fuel for furnaces in past time, which represents a great waste of useful resource. The use of ethylene in dry gas to produce ethylbenzene will extend the of ethylene source, open up a new way of comprehensive utilization of dry gas and obviously increase economic effectiveness.

In recent decades, the use of dilute ethylene for ethylbenzene production has drawn a widespread attention in the world and has achieved rapid progress. The common processes for ethylbenzene production by the alkylation of benzene with ethylene fall roughly into two categories, one is gas-phase method, and the other is liquid-phase method. In gas-phase method both ethylene and benzene are kept in gas phase and the alkylation to ethylbenzene is proceeded over a solid catalyst, which belongs to gas-solid reaction type and has a long history of industrial application. The recent representative process of gas phase method is Mobil/Badger technology, which was developed by Mobil Oil Company and Badger Engineering Company in 1970s and got continued improvement later. Hydrocarbon Processing (Part of Petrochemical Processes'95, March 1995, page 115) reported the third generation of process for the ethylbenzene preparation by gas-solid phase alkylation of benzene with dilute ethylene contained in dry gas which took over ZSM-5 zeolite. EP-0308099 disclosed a process for the preparation of ethylbenzene by gas-phase alkylation over ZSM-5 zeolite, and a process for the transalkylation of benzene with diethylbenzene to ethylbenzene over ZSM-5 and ZSM-11 zeolites. The main advantages of the gas-phase method are as follows: ethylene stock needs not to be in a high purity, it is suitable for various ethylene sources and various content of ethylene in the range of 10–100% by mole, high catalyst capacity, no corrosion and pollution, simple technological process with high utilization of energy. But the gas phase process also has obvious disadvantages: rigorous control of the concentration of harmful impurity such as $H_2S$, $O_2$, $CO_2$, $H_2O$ etc. in dry gas below 1 ppm, high reaction temperature and middle pressure, for example, the alkylation needs to be operated at 300–500° C. and 0.1–20.8 MPa, as described in the above patents, which leads to high energy consumption, strict requirements for the apparatus and for the operation. Moreover, the reaction produces more by-products, the ethylbenzene selectivity is not high, ZSM-5 zeolite is more likely to deactivate by coking, the concentration of dimethylbenzene in product ethylbenzene amounts to 1000–2000 ppm (industry required below 100 ppm) which negatively affects the quality of polystyrene.

In addition, CN 1031072A (applicant: No. 2 petroleum works, Fushun Petrochemical Company, China) and CN 1074392A (applicant: Dalian chemical physics institute, Chinese Science Academy) also reported the modified commercial ZSM-5 catalyst and its preparation. When used for gas-phase alkylation to produce ethylbenzene, the ZSM-5 catalyst is likely to deactivate by coking due to high reaction temperature, and the concentration of dimethylbenzene in the product mixture is high, which make the disadvantages of the gas phase method mentioned above unavoidable.

Another kind of process for the alkylation of benzene with ethylene to produce ethylbenzene is called liquid-phase method, in which both ethylene and benzene are kept in liquid phase under high pressure and the alkylation reaction takes place over a solid catalyst. The liquid phase method belongs to liquid-solid reaction type.

The representative process of liquid-phase method is Unocal/Lummus/UOP technology which produces ethylbenzene by liquid-phase alkylation of benzene with ethylene over a solid acid catalyst containing Y zeolite. Compared with gas-phase method, the liquid-phase method has the following features: the reaction takes place in liquid phase, the temperature is generally below 300° C., the lifetime of catalyst is long, the selectivity of ethylbenzene is high, the concentration of dimethylbenzene in product ethylbenzene is just below 100 ppm, which fully satisfies the requirement for high quality styrene. Hereafter, many publications reported the improvement of the process for liquid-phase alkylation for ethylbenzene production and the catalyst and its preparation. For instance:

G. Bellussi et al (Journal of Catalysis, 1995, 157, 227–234) disclosed that β zeolite had higher activity and selectivity than that of Y zeolite in the liquid-phase alkylation of benzene, and proposed a mechanism wherein the activity of β zeolite was controlled by internal diffusion within particles. This reference only discussed general questions of liquid-phase benzene alkylation with lower olefin, and compared the activities and selectivities of various zeolites of different types.

Hydrocarbon Processing (Part of Petrochemical Processes'95, March 1995, page 114) reported Unocal/Lummus/UOP process in which fixed bed was used to produce ethylbenzene by liquid phase alkylation over a zeolite, but it didn't relate to the specific catalyst and operation conditions.

U.S. Pat. No. 5,145,817 (Dow Chemical Company) described a bimetal ultrastable Y-type zeolite used in the liquid-phase alkylation and transalkylation of benzene to produce ethylbenzene, in which the pressure of the reactor was 35 atm and the temperature was 223–301° C.

U.S. Pat. No. 5,030,786 (Fina Technology Company) relates to a process for alkylation/transalkylation of aromatics to produce ethylbenzene, in which dehydrated aromatics was fed into the reaction zone containing zeolite catalyst to carry out a liquid reaction over one of Y, Ω and β zeolites at a temperature of 225° C. and a pressure of 24.5 atm.

CN 1096470A described a kind of β-zeolite/γ-alumina catalyst used for liquid-phase benzene alkylation, in which 0.5–10% by weight, preferred 1–5% by weight fluorine or chlorine was incorporated so as to improve the activity of catalyst. In its example 4, the condition of 200° C. and 2.94 MPa was used to evaluate catalyst.

Although liquid phase method takes outstanding advantage over gas phase one, it also has obvious weakness. The reaction pressure of liquid phase method is far greater than that of gas-phase method, which leads to increase of energy consumption, complexity in apparatus and in operation. The more unfavorable is that the liquid-phase method requires pure ethylene as feed and dilute ethylene is not usable, so liquid phase method can not be adopted to produce ethylbenzene using dilute ethylene stock.

In addition to the gas phase method and liquid-phase method, CN 1207960A (applicant: No.2 Chemical Works, Beijing Yanshan Petrochemical Corporation and Beijing Institute of Clothing Technology) reported a new process for gas-liquid phase alkylation of benzene with dilute ethylene contained in refinery dry gas to produce ethylbenzene over a new β zeolite catalyst, in which benzene was fed in liquid-phase while dry gas was fed in gas phase, two feeds countercurrently flowed through the reactor and reacted over the catalyst in the fixed bed, the product mixture was drawn from the reactor and was separated to obtain ethylbenzene. Belonging to gas-liquid-solid three phase reaction type, the process combines the main advantages of the gas-phase method and the liquid-phase method. The temperature and pressure in gas-liquid-solid process are both low, the requirements for apparatus and operation is not strict, both the conversion of ethylene and selectivity of ethylbenzene are high, the concentration of dimethylbenzene in product is very low, and the lifetime of catalyst is long. The more important is that the gas-liquid-solid process may use dilute ethylene as feed. However it seems that the process needs improvement, due to high external reflux ratio which leads to heavy burden for separating benzene and ethylbenzene, high molar ratio of benzene to ethylene in feed which limits the catalyst capacity, and the selectivity of the product ethylbenzene also needs to be enhanced, etc.

U.S. Pat. No. 5,476,978 disclosed a process for the alkylation of benzene with ethylene to produce ethylbenzene by catalytic distillation, in which ethylene and benzene in excessive amount were respectively fed into the catalytic distillation tower to take alkylation reaction and distillation separation simultaneously. The process takes advantages of catalytic distillation, and the extent of catalyst utilization and product quality is high. However the process uses almost pure ethylene, so the gas flux is not large, and so liquid flooding in tower could be easily avoided. Hence there are not too much requirements for the similarity of the catalyst and the packing particles in respect of their size, structure and bulk density of the catalyst particle and the packing, neither for bed voidage. In its example, the catalyst particles were tilled in small pockets of fiber glass belts and set in a helix form with stainless steel mesh, then packed in reaction zone layer by layer. The process is not suitable for dilute ethylene feed because large amount of other gases such as $N_2$, $CO_2$, $H_2$, and $C_{1-4}$ paraffins will lead to a large gas flux, more likely flooding and thus to a difficult gas-liquid mass transfer. Then high bed voidage and high efficiency of mass transfer between catalyst particles and packing are required and it is difficult to satisfy in this patent.

There has been existing a need to provide an improved method for the preparation of ethylbenzene by alkylation of benzene with dilute ethylene contained in the dry gas, in which the moderate reaction conditions and simple and inexpensive operation can be used to utilize the dilute ethylene in refinery dry gas to produce ethylbenzene in high purity with high conversion of ethylene, high selectivity of ethylbenzene, high quality of product and long catalyst lifetime.

Therefore, one object of the invention is to provide a new method for the preparation of ethylbenzene by alkylation of benzene with dilute ethylene contained in refinery dry gas.

Another object of the invention is to provide an apparatus which can be used in the process for the preparation of ethylbenzene by alkylation of benzene with dilute ethylene contained in refinery dry gas.

SUMMARY OF THE INVENTION

The process for the preparation of ethylbenzene by alkylation of benzene with dilute ethylene in refinery dry gas, according to the invention is carried out within a catalytic distillation tower which consists of a reboiler, a stripping section, a reaction section, an optional rectifying section and a top condenser. During the operation, by adjusting the parameters of reaction section and tower, some of benzene and product ethylbenzene and heavy by-products are kept in liquid phase in the tower, ethylene and other components in dry gas are kept in gas phase, benzene and dry gas are countercurrently fed into the tower respectively to allow alkylation reaction to produce ethylbenzene within the bed packed with catalyst and packing in the tower, meanwhile the unreacted components in dry gas, benzene and products take distillation separation in the tower. The process belongs to gas-liquid-solid three phases type with catalytic reaction and distillation separation taking place simultaneously, comprising the features as follows:

1) Refinery dry gas is pretreated by, if necessary, adjusting pressure, desulfurization, and dehydration.

2) Pretreated dry gas is fed into a catalytic distillation tower at a position below the reaction section, benzene is fed into the top of the tower, or split to several streams and fed into the top of the tower and different position of the reaction section according to practical needs; With the total molar ratio of benzene to ethylene in feeds being in the range of 5–20, the two feeds are kept countercurrently flowing in the tower and reacting with each other inside the reaction section which is packed with catalyst/distillation packing particles, and the mixture of reactants and products are separated by distillation simultaneously; The top overhead comprises vaporized benzene and residual components in the dry gas, while the bottoms consist of liquid mixture containing product ethylbenzene.

3) The reaction section packed with catalyst particles and distillation packing should meet the following conditions:
 (a) The catalyst used satisfies:
  evaluated ethylene conversion$\geq 95\%$, and
  evaluated ethylbenzene selectivity$\geq 95\%$;
 (b) The separating efficiency of the reaction section satisfies:
  $\geq 0.5$ theoretical stage per meter of measuring tower (catalyst particles+distillation packing)
 (c) The bed voidage of reaction section is $\geq 70\%$.

Common random packing and structured packing can be used in the stripping section and the optional rectifying section, provided that the prerequisite of separating efficiency greater than 1 theoretical stage per meter of measuring tower is met. The same distillation packing as used in reaction section is preferred.

DESCRIPTION OF THE INVENTION

Referring to the attached figures, the following will describe the invention in detail.

Figure 1:
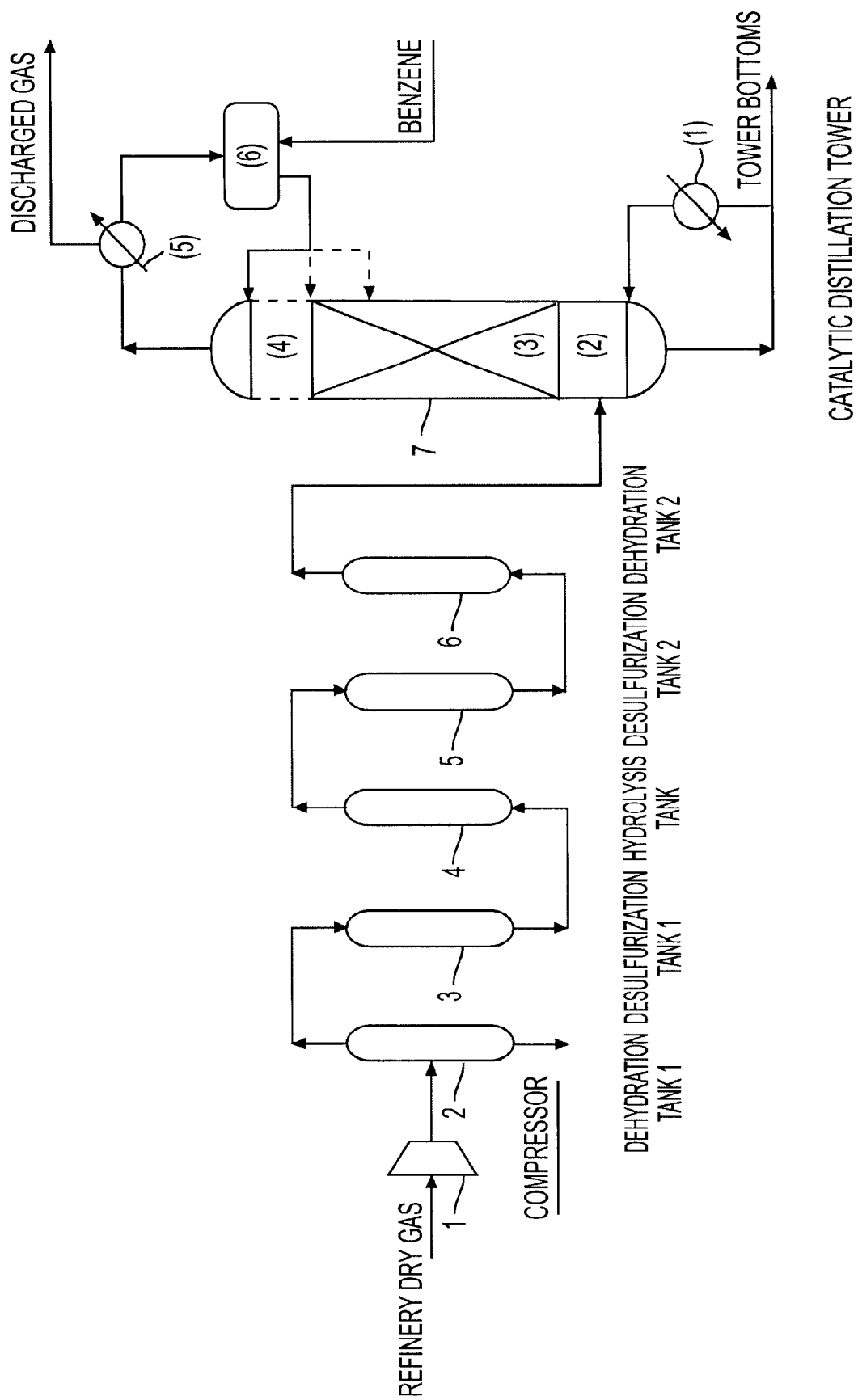
FIG. 1 is a schematic representation of the process for the preparation of ethylbenzene by alkylation of benzene with dilute ethylene contained in refinery dry gas according to the invention.

According to FIG. 1, the processing steps from entery of refinery dry gas into boundary area till before it's feeding into the catalytic distillation tower belong to the dry gas pretreatment section 1) mentioned above, including the following processing steps: the dry gas coming from refinery at a pressure of 0.3–0.7 MPa, containing 10–30% ethylene and other components such as hydrogen, nitrogen, oxygen, water, methane, ethane, propylene and butene, is compressed to 2.5–3.0 MPa by pressure adjusting apparatus 1 such as compressor; most saturated water is removed from the compressed dry gas in the first dehydration tank 2; dehydrated dry gas flows into the first desulfurization tank 3, wherein most of $H_2S$ are removed by FeO; then the dry gas enters into hydrolysis tank, wherein COS in dry gas can be converted into $H_2S$ which is adsorbed by adsorbent such as ZnO in the second desulfurization tank 5, then the concentration of $H_2S$ in discharged dry gas is less than 5 ppm, other organic sulfur compounds have no influence on catalyst; desulfurized dry gas enters the second dehydration tank 6 which may consists of two alternative ones using 3 Å molecular sieve that can be reused by regeneration under the temperature 250° C.; the concentration of water in dehydrated dry gas is below 30 ppm, then the pretreated dry gas is fed into the catalytic distillation tower 7 at a position below the reaction section.

Because benzene can absorb water at the atmospheric conditions, so it should be dehydrated by 3 Å molecular sieve or azeotropic distillation, both of which is capable of removing the water in the benzene feed to a concentration below 100 ppm; dehydrated benzene together with refluxing benzene from condenser and other benzene, if any, are fed into the top of the catalytic distillation tower, or split to several streams and fed into the top of the tower and different positions of the reaction section, according to practical need.

The reaction among the reactants and the distillation separation of the products are carried out in catalytic distillation tower 7. Referring to FIG. 1, tower 7 consists of a bottom reboiler(1), a stripping section(2) located at lower part, a reaction section(3) located above the stripping section (2), a optional rectifying section(4) located above the reaction section(3), a top condenser(5) and a reflux tank(6). The stripping section and optional rectifying section are packed only with distillation packing, the reaction section is packed with catalyst particles and distillation packing. The materials in the tower are kept in gas- and liquid phase by adjusting the temperature and pressure of tower, meanwhile the catalyst is maintained active. The pretreated dry gas is fed into the tower at one stage of the stripping section after metering, while benzene in a single stream or, if necessary, being divided into several streams is fed into the top of the rectifying section, or into the top of the reaction section or several different feeding positions if rectifying section is not used. The gas phase feed and the liquid phase feed countercurrently contact and react each other in the reaction section, and the distillation separation of product mixture is taken place simultaneously. The heat from reaction and from reboiler vaporizes some of liquid benzene, and the vaporized benzene, together with the residual components in dry gas, flowes upwards and enters into top condenser from the top of reaction section, or from the top of rectifying section, if existed. The condensated benzene, together with fresh benzene or other benzene sources are returned to the catalytic distillation tower as feed, the dry gas residues are sent to post-treatment or low pressure gas pipeline after metering and chromatographic analysis, the liquid mixture containing mainly benzene and ethylbenzene is obtained from tower bottom and then is sent to post treatments.

According to the invention, the reaction section must satisfy the third requirements as described above, wherein any kinds of catalyst satisfying the requirement can be used. When benzene is kept in liquid phase and dry gas is kept in gas phase, the catalyst should have enough activity, high product selectivity and high ethylene conversion, which is one of basic requirements for smoothing embodiment of the invention. The catalyst can be made into common shapes such as sphere, sheet, pellet, strip, etc. But in order to improve its performance as reacting unit and distillation unit, it is preferred to make the catalyst into complicated shapes, such as Raschig ring, trifolium, θ ring, cross cylinder, multi-hole cylinder, etc. The θ ring and cross cylinder are preferred, of which the suit particle size is $\phi 3$–6 mm.

Similarly, any packing and loading method of the catalyst particles and the packing satisfying the said requirements can be used in the reaction section, which keeps enough mass transfer capacity in the catalyst/distillation packing bed, provides enough surface area for dissolving and absorbing of ethylene into liquid benzene, separates the formed ethylbenzene downwards so as to leave the reaction section quickly, increases the selectivity of product ethylbenzene and the catalyst capacity while decreases the formation of by-products such as diethylbenzene and dimethylbenzene. The distillation packing can be made of any materials which are inert to the reaction system under the tower conditions, such as metal, stainless steel, ceramics, etc. The type of packing can be various, including conventional and special types. The specific type is determined by the catalyst shape, in order to keep the structure and size of the packing in accord with the shape and size of the catalyst, which enables the catalyst bed to perform the reaction and distillation function all very well. The packing can be random one, such as Raschig ring, θ ring, cross cylinder, etc., the θ stainless steel Cannon ring is preferred. The packing can also be structured one, such as stainless steel structured packing plate with corrugated configurations.

The requirement for bed voidage$\geq 70\%$ is made so as to avoid possible flooding when refinery dry gas is used. Any type, size, and loading way of catalyst and of packing satisfying the requirement for bed voidage is usable in the invention.

According to the invention, the operation conditions of the tower such as reaction temperature, pressure, benzene WHSV, reflux ratio, molar ratio of benzene to ethylene, catalyst loading fraction, can be determined according to the type and loading way of catalyst and packing used. In general, the reaction temperature should be capable of keeping the catalyst in its active state, the preferred temperature is 130–190° C. The reaction pressure should be in accord with temperature. On the condition of maintaining a high ethylene conversion, the lower the pressure is, the higher the ethylbenzene selectivity and product purity will be. The preferred pressure is 1.5–2.0 MPa. An increase of total molar ratio of benzene to ethylene would lead to an increase of either ethylene conversion and ethylbenzene selectivity. Especially when the concentration of ethylene in dry gas is low, a larger total molar ratio of benzene to ethylene is needed. But when this ratio is too large, the load of tower and the expenditure of energy will be increased inappropriately, so the total molar ratio of benzene to ethylene in feed should be in the range of 5–20, the preferred one is in the range of 8–12. In fresh feeds, the molar ratio of benzene to ethylene should be in the range of 1–3; benzene's WUSV should be 2–3 $h^{-1}$. Depending on catalyst activity, selectivity, size and shape, the catalyst loading fraction should enable a quick reaction between benzene and ethylene which have been transferred to the active surface of the catalyst, so as to synthesize ethylbenzene. The specific amount can be obtained by experiment, usually the catalyst loading fraction is 5–40%, the preferred is 15–25%. The reflux ratio is controlled by the heat from the reaction and the from reboiler. During the operation, some of liquid benzene vaporize upon taking the heat from reaction and from reboiler, which are condensated to liquid again in the condenser and then return totally to the tower as reflux, thus an internal recycle of benzene is established in the tower. The recycle can increase the total molar ratio of benzene to ethylene during the reaction, make the concentration of benzene far greater than that of ethylene, increase ethylene conversion and inhibit deep alkylation.

In the invention, the following special terms are defined as follows;

The evaluation of the performances of both the catalyst and the packing are conducted outside the catalytic distillation tower.

Catalyst:

The performance of catalyst is evaluated by differential reactor. The evaluating conditions are as follows; catalyst 10 g, benzene WHSV 2 $h^{-1}$, feed molar ratio of benzene to ethylene 8:1, temperature 160° C., pressure 1.8 MPa. The ethylene conversion and ethylbenzene selectivity are calculated from the analysis data of feed and products by the following formulas, the two parameters obtained and calculated under the said conditions are prefixed with "evaluated".

Ethylbenzene conversion: $X_E=(F_{EI}-F_{E0})/F_{EI}*100\%$

Where:

$F_{EI}$—molar flow of ethylene in pretreated dry gas, mol/h
$F_{E0}$—molar flow of ethylene in discharged gas, mol/h Ethylbenzene selectivity $S_E=[EB]/([EB]+[DEB])*100\%$ Where:

[EB]—molar concentration of ethylbenzene in tower bottoms

[DEB]—molar concentration of diethylbenzene in tower bottoms

Measurement of theoretical stage:

The theoretical stage of distillation packing or catalyst/distillation packing bed may be measured by distillation test. The materials to be measured are put into the distillation tower which consists of tower body, reboiler, condenser. The materials used for this measurement may be binary mixture such as benzene-toluene, benzene-phenixin, etc. First of all, the materials used is put into the bottom of the packing tower, and adjust the heat provided by the reboiler, operate the tower in total reflux way under normal pressure for about one and a half hour. When gas phase and liquid phase reach equilibrium, the compositions of gas- and liquid phase in both the top and bottom of the tower are measured, then calculate theoretical stages in total of packing by graphic method or shortcut method. Divided by the height of packing or bed, the theoretical stage per meter of packing or bed can be obtained from the total theoretical stages.

Bed voidage of reaction section is measured as follows:
Deposit the catalyst/distillation packing into the reaction section, seal the bottom, leave the top open, weigh the object; then add water into the reaction section until the packing is submerged, weigh the object again; the difference of two weights is the weight of added water. The volume of added water is the void volume of the bed, which is then divided by volume of the whole bed, with the bed voidage value being obtained.

Reaction pressure refers to the pressure of catalytic distillation tower;

Pressure drop of tower refers to the difference between the pressures at the top and bottom of catalytic distillation tower;

Benzene WHSV refers to the weight of benzene per unit catalyst weight per hour;

Reflux ratio refers to the molar ratio of benzene reflux from the tower top to fresh benzene;

Total molar ratio of benzene to ethylene refers to the molar ratio of total benzene feeding into catalytic distillation tower(including fresh benzene, benzene reflux and recycle benzene, if existed) to ethylene in dry gas feed;

Molar ratio of benzene to ethylene refers to the molar ratio of fresh benzene to ethylene in dry gas feed;

Catalyst loading fraction refers to the volume fraction of catalyst in the reacting bed packed with catalyst particles/distillation packing.

According to the invention, not only the ethylene in dry gas can be fully utilized in alkylation with benzene to obtain ethylbenzene, but also the propylene(usually 1–5%) in dry gas can take part in alkylation with benzene to synthesize cumene which is obtained from tower bottoms. A cumene tower can be added in subsequent separation steps to produce valuable cumene.

Figure 2:
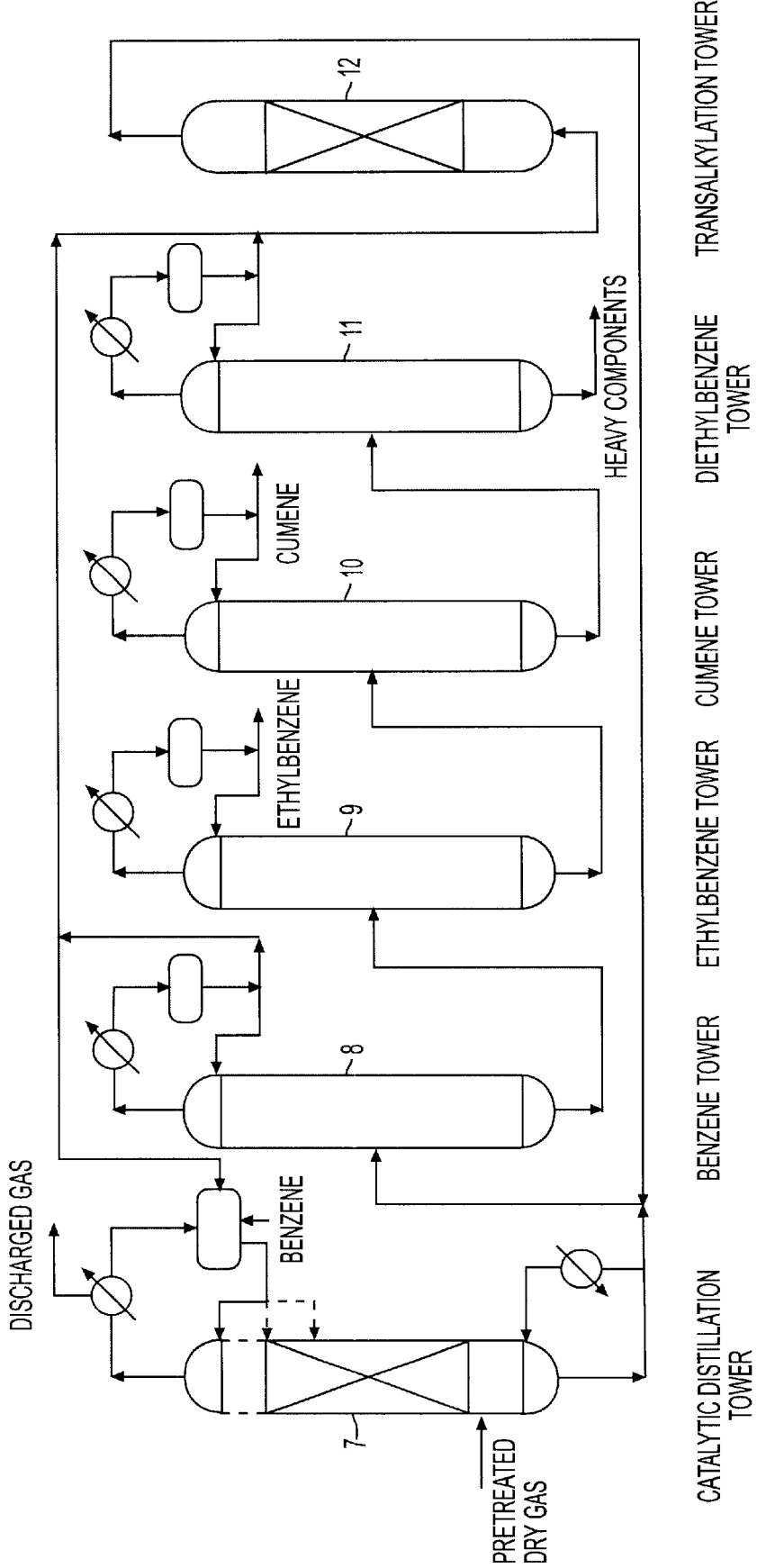
FIG. 2 is schematic of optimized design on the basis of FIG. 1, with residue separation and transalkylation.

According to a preferred embodiment of the invention, the post-treatment for tower bottoms is added. Referring to FIG. 2(pretreatment for dry gas omitted, which is the same with FIG. 1), the catalytic distillation tower bottoms are fed into benzene tower 8, where benzene is separated from other heavy components and obtained in top condenser, then the benzene is fed to catalytic distillation tower 7 and transalkylation tower 12. The benzene tower bottoms are fed into ethylbenzene tower 9 to separate product ethylbenzene, and the bottoms from tower 9 are fed into cumene tower 10 to recover cumene which is formed by the alkylation of benzene with propylene (1–5% in dry gas) over the catalyst. The bottoms from tower 10 are fed into diethylbenzene tower 11, the heavy components are recovered as tower bottoms and sent to other processes or burnt, the diethylbenzene is recovered as overhead. Then the diethylbenzene is fed into transalkylation tower 12 to take transalkylation reaction with benzene from tower 8 to produce ethylbenzene, the mixture of products are fed to the separation process.

Figure 3:
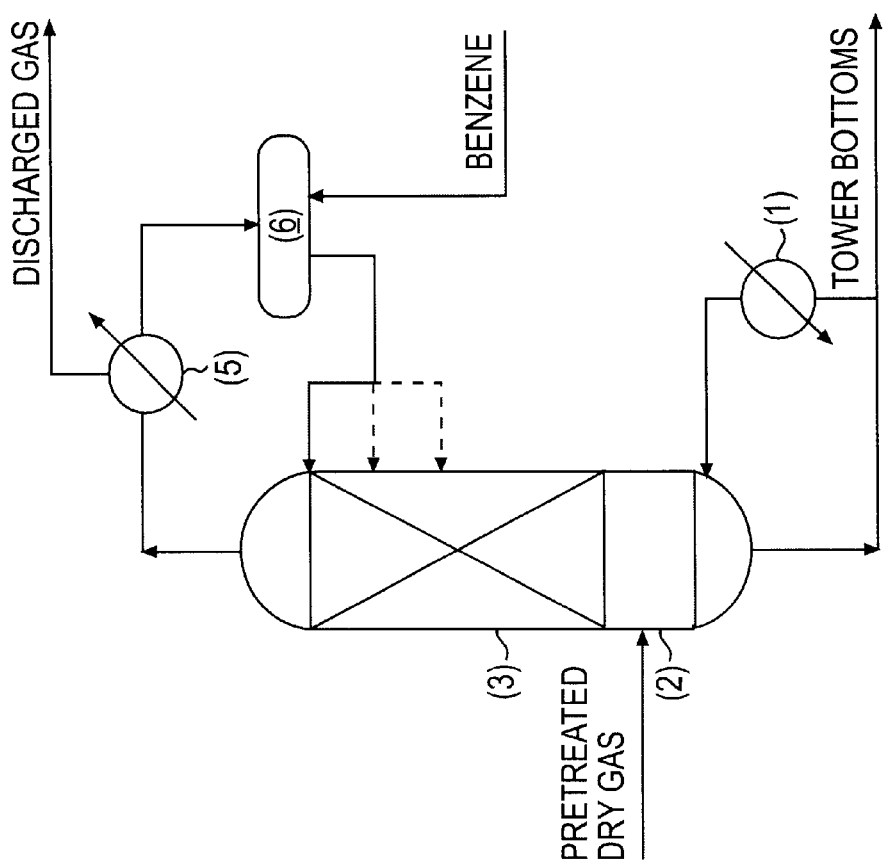
FIG. 3 is an abridged view of a preferred embodiment of catalytic distillation tower which was packed with well-distributed catalyst particles and distillation random packing according to the invention, wherein rectifying section is omitted.

According to a further preferred embodiment of the invention (referring to FIG. 3), in addition to satisfying the requirements 1)–3) prescribed above, in the reaction section of catalytic distillation tower, the distillation packing is stainless steel θ Cannon ring with external diameter φ4 mm the catalyst is β zeolite which is formed in to φ4 mm cross cylinder and mixed in 20% loading fraction with the above θ stainless steel Cannon rings, and then filled the mixture into the reaction section and form catalyst/distillation packing bed of the invention. The reaction section has excellent performance for catalytic reaction and distillation separation, so there is almost no ethylene found in the upwards gas leaving the reaction section, and there is almost no ethylbenzene found in the liquid near the top of the reaction section, therefore the rectifying section may be omitted, the tower structure and operation is more simplified.

Referring to FIG. 1, the apparatus suitable for the invention comprises some devices for pretreatment of dry gas and other devices for catalytic alkylation of benzene with ethylene and distillation. The former ones comprise a pressure adjusting device 1, a first dehydration device 2, a first desulfurization device 3, hydrolysis device 4, a second desulfurization device 5 and the second dehydration device 6. The latter ones are mainly composed of catalytic distillation tower 7 which consists of a reboiler(1), a stripping section(2), a reaction section(3), an optional rectifying section(4), a top condenser(5) and a reflux tank(6), and relevant pipelines, metering and conveying device for benzene, dry gas and for the bottoms.

Referring to FIG. 2, the apparatus of the invention may also include additional devices for separation of the product mixture drawn from tower bottom and further additional devices for transalkylation, consisting of a benzene tower 8 used for benzene separation from the product mixture; an ethylbenzene tower 9 used for recovering ethylbenzene at the tower top; a cumene tower 10 used for recovering cumene at the tower top; a diethylbenzene tower 11 used for recovering diethylbenzene at the tower top; and a transalkylation tower 12 used for conducting transalkylation of benzene coming from benzene tower 8 with diethylbenzene coming from diethylbenzene tower 11, and the product mixture are returned to benzene tower via pipeline for separation.

According to the invention, the process for the preparation of ethylbenzene by alkylation of benzene with ethylene within a catalytic distillation tower has outstanding advantages. The process is a coordinating course of gas-liquid-solid three phases reaction and distillation separation. The alkylation reaction and the distillation separation are carried out simultaneously within one tower, which simplifies apparatus, contributes to the movement of reaction equilibrium towards formation of products, increases the catalyst capacity and product selectivity, also makes full use of the reaction heat for distillation, and decreases the energy consumption obviously. Moreover, the process combines the main advantages of gas-phase method and liquid-phase method, such as a moderate reaction condition, low temperature and pressure, large catalyst capacity, long lifetime per run, high product selectivity and purity, low load of post-treatment, etc.

The following will give a detailed explanation of the invention in the light of examples, but it doesn't mean any limitation for the invention. An ordinary technician in the art may make many changes and improvements based on the disclosed contents of the invention, such as using other dilute ethylene sources as feed, but all these changes and improvements will fall within the spirits of the invention determined by the attached claims.

EXAMPLE 1

An apparatus as shown in FIG. 1 was used. Except for the catalytic distillation tower, the other devices were all conventional. The catalytic distillation tower used was shown in FIG. 3, the inner diameter of the tower was φ30 mm. The tower didn't have rectifying section. The reaction section was packed with β zeolite-based FX-02 catalyst which was developed by Beijing Institute of Clothing Technology and Beijing HuaYuTongFang Chemical Science and Technology Development Company Limited. (HYTF) and produced by HYTF. The catalyst was formed in to φ4 mm. cross cylinder and was mixed with φ4 mm stainless steel θ Cannon rings, then loaded into the reaction section with the catalyst loading fraction of 20%.

Evaluated by the method described above, the catalyst had the following performance: evaluated ethylene conversion was 96%, evaluated ethylbenzene selectivity was 98%; the catalyst/distillation packing bed possessed 7 theoretical stages per meter of measuring tower; the bed voidage was 75%.

A kind of catalytic cracking dry gas was used as gas feed, the composition of the dry gas was shown in Table 1.

TABLE 1

| component | \multicolumn{12}{c}{Composition of the dry gas} |
|---|---|---|---|---|---|---|---|---|---|---|---|---|
| component | $H_2$ | $CO_2$ | $N_2 + O_2$ | $CH_4$ | $C_2H_6$ | $C_2H_4$ | $C_3H_8$ | $C_3H_6$ | $C_4H_{10}$ | $C_4H_8$ | $H_2O$ | $\Sigma S$ |
| mol % | 15.0 | 3.6 | 12.9 | 30.7 | 15.4 | 17.0 | 0.9 | 1.4 | 0.7 | 0.17 | 10400 ppm | 120 ppm |

After pretreated, the composition of the dry gas feed almost didn't change before fed into catalytic distillation tower, but the concentration of water was reduced to 20 ppm, total sulfur content was about 10 ppm, wherein $H_2S$ content was below 5 ppm.

The operation conditions of the tower were as follows: tower bottom temperature 235±5° C., reaction section temperature: the upper part 135±3° C., the middle part 155±3° C., the lower part 160±3° C.; condenser outlet temperature 30° C.; pressure 1.59 MPa, benzene WHSV 2 $h^{-1}$, molar ratio of benzene to ethylene in fresh feed 2.5.

The composition of the tower bottoms was shown in Table 2.

TABLE 2

| component | B | EB | DEB | C9 | C10 |
|---|---|---|---|---|---|
| mol % | 73.31 | 23.23 | 0.82 | 3.79 | 1.21 |

The concentration of ethylene in discharged gas at the tower top was 0.69% (mol) by chromatography analysis, the ethylene conversion was 96.4%, the ethylbenzene selectivity was 96.6%, the catalyst capacity amounted to 10,000 tons ethylbenzene per ton of catalyst per year.

EXAMPLE 2–7

The same apparatus was used as Example 1, the concentration of ethylene and some operation conditions were changed(see Table 3) to obtain a series of test results of the process for the preparation of ethylbenzene from ethylene by catalytic distillation, the results were shown in Table 3.

TABLE 3

Results of different ethylene content and operation conditions

| Example No. | 2 | 3 | 4 | 5 | 6 | 7 |
|---|---|---|---|---|---|---|
| Ethylene content in dry gas(%) | 12 | 16 | 16 | 12 | 16 | 16 |
| Benzene WHSV($h^{-1}$) | 2 | 2 | 2 | 2 | 2 | 2 |
| Ratio of benzene to ethylene | 3 | 2 | 2 | 2.5 | 2.5 | 2.5 |
| Pressure(MPa) | 2.0 | 2.0 | 2.0 | 2.0 | 2.0 | 1.8 |
| Ethylene content in discharged gas(%) | 0.595 | 1.233 | 0.614 | 0.615 | 0.302 | 0.679 |
| Ethylene conversion(%) | 95.61 | 93.44 | 96.75 | 95.46 | 98.41 | 96.41 |
| Composition of tower bottoms(%) | | | | | | |
| Ethylbenzene | 30.518 | 40.464 | 35.519 | 33.814 | 33.533 | 35.210 |
| Diethylbenzene | 1.677 | 2.770 | 2.757 | 2.471 | 2.284 | 1.864 |
| Ethylbenzene selectivity(%) | 94.79 | 93.59 | 92.80 | 93.19 | 93.62 | 94.97 |
| Catalyst loading fraction(%) | 25 | 25 | 20 | 20 | 20 | 20 |

What is claimed is:

1. A process for the preparation of ethylbenzene by alkylation of benzene with dilute ethylene contained in a refinery dry gas by catalytic distillation, which is carried out within a catalytic distillation tower comprising a reboiler, a stripping section, a reaction section, an optional rectifying section, and a top condenser, which process comprises 1) pre-treating a raw refinery dry gas by, if necessary, pressure adjusting, desulfurization and dehydration, resulting in a pre-treated dry gas;

2) feeding the pre-treated dry gas into a catalytic distillation tower at a position below the reaction section, and feeding benzene into the tower at its top, or splitting benzene feed into several streams and feeding them into the tower at its top and at different positions of the reaction section, the total molar ratio of total benzene to total ethylene being in the range of 5–20, and the molar ratio of benzene/ethylene in the fresh benzene and dry gas feeds being 1–3; keeping the benzene and dry gas feeds countercurrently flowing in the tower and reacting with each other inside the reaction section which is packed with a bed of catalyst particles and distillation packing, and simultaneously separating in the reaction section the resulting mixture of reactants and products by distillation; drawing out of the tower the top overhead and the bottoms comprising product ethylbenzene; condensing vaporized benzene in the top overhead in the top condenser; and recycling the condensed benzene to the tower;

3) wherein the reaction section packed with catalyst particles and distillation packing meets the following conditions:

(a) the catalyst used satisfies:
         evaluated ethylene conversion $\geq 95\%$, and
         evaluated ethylbenzene selectivity $\geq 95\%$;

(b) the separating efficiency of the reaction section satisfies:
         $\geq 0.5$ theoretical stage per meter of measuring tower (catalyst particles+distillation packing); and (c) the bed voidage of the reaction section is $\geq 70\%$.

2. Process according to claim 1, wherein the raw refinery dry gas contains ethylene in the amount of from 10 to 20% by weight.

3. Process according to claim 1, wherein the reaction section has a catalyst loading fraction of from 5 to 40% by volume of the reaction section.

4. Process according to claim 1, wherein the catalyst and the distillation packing are shaped into at least one form selected from the group consisting of spheres, pellets, trifoliums, Raschig rings, cross cylinders, and multi-hole cylinders.

5. Process according to claim 4, wherein the catalyst is a β zeolite-based catalyst.

6. Process according to claim 5, wherein the catalyst is mixed intimately with the distillation packing and then packed into the reaction section with the catalyst loading fraction being about 20% by volume of the reaction section.

7. Process according to claim 6, wherein the catalyst and the distillation packing are shaped into cross cylinder and a θ cannon ring, respectively.

8. Process according to claim 1, wherein the reaction section is operated at the conditions of a pressure of 1.5–2.0 MPa, a reaction temperature of 130–190° C., and a benzene WHSV of 2–3$h^{-1}$.

9. Process according to claim 8, further including conducting an alkylation of benzene with propylene contained in the dry gas, which is conducted simultaneously in the catalytic distillation tower.

10. Process according to claim 9, further comprising separating diethylbenzene from a liquid product mixture drawn from the bottom of the catalytic distillation tower and a step of transalkylating the separated diethylbenzene with benzene.

11. The process of claim 1, wherein the catalyst particles and distillation packing in the reaction section are mixed.

* * * * *